(12) United States Patent
Kwun et al.

(10) Patent No.: US 6,373,245 B1
(45) Date of Patent: *Apr. 16, 2002

(54) METHOD FOR INSPECTING ELECTRIC RESISTANCE WELDS USING MAGNETOSTRICTIVE SENSORS

(75) Inventors: Hegeon Kwun; Sang Young Kim, both of San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/666,752

(22) Filed: Sep. 21, 2000

Related U.S. Application Data

(63) Continuation-in-part of application No. 09/519,530, filed on Feb. 25, 2000, now Pat. No. 6,294,912.
(60) Provisional application No. 60/124,763, filed on Mar. 17, 1999.

(51) Int. Cl.$^7$ .......................... G01N 27/82; G01N 29/04; G01N 9/24; G01R 33/12
(52) U.S. Cl. .......................................... 324/240; 73/643
(58) Field of Search .................. 324/238, 239, 324/240, 242, 260, 209; 73/598, 624, 629, 643

(56) References Cited

U.S. PATENT DOCUMENTS 5,537,876 A * 7/1996 Davidson et al. ............. 73/624
6,294,912 B1 * 9/2001 Kwun ........................ 324/240

* cited by examiner

Primary Examiner—Walter E. Snow
(74) Attorney, Agent, or Firm—Gunn, Lee & Hanor

(57) ABSTRACT

A method and apparatus is shown for implementing magnetostrictive sensor techniques for the nondestructive evaluation of plate type structures such as walls, vessels, enclosures, and the like. The system includes magnetostrictive sensors specifically designed for application in conjunction with plate type structures or pipes that generate guided waves in the plates or pipes which travel therethrough in a direction parallel to the surface of the plate or pipe. Similarly structured sensors are positioned to detect the guided waves (both incident and reflected) and generate signals representative of the characteristics of the guided waves detected that are reflected from anomalies in the structure such as corrosion pits and cracks. The sensor structure is longitudinal in nature and generates a guided wave having a wavefront parallel to the longitudinal axis of the sensor, and which propagates in a direction perpendicular to the longitudinal axis of the sensor. The generated guided waves propagate in the plate within the path of the propagating wave. The reflected waves from these abnormalities are detected using a magnetostrictive sensor. Shear horizontal waves may also be created by rotating the magnetic bias 90° and used for similar inspection techniques. Pipes, which act as curved plates, may also be inspected as well as electric resistance welds therein. In addition, steel sheet butt welds may be inspected with this technique.

12 Claims, 10 Drawing Sheets

METHOD FOR INSPECTING ELECTRIC RESISTANCE WELDS USING MAGNETOSTRICTIVE SENSORS

This is a continuation-in-part patent application depending from U.S. patent application Ser. No. 09/519,530, filed on Feb. 25, 2000, now U.S. Pat. No. 6,294,912, which depends from provisional Patent Application Serial No. 60/124,763, filed on Mar. 17, 1999.

BACKGROUND OF THE INVENTION

1. Field of the Invention

The present invention relates generally to methods and devices for the nondestructive evaluation of materials. The present invention relates more specifically to the use of magnetostrictive sensors to inspect electric resistance welds.

2. Description of the Related Art

Magnetostrictive effect refers to the phenomena of a physical dimension change in ferromagnetic materials that occurs through variations in magnetization. In magnetostrictive applications, the generation and detection of mechanical waves is typically achieved by introducing a pulse current into a transmitting coil adjacent to a ferromagnetic material. The change in magnetization within the material located near the transmitting coil causes the material to change its length locally in a direction parallel to the applied field. This abrupt local dimension change, which is the magnetostrictive effect, generates a mechanical wave that travels at the speed of sound within the ferromagnetic material. When the mechanical wave is reflected back from the end of the ferromagnetic material, or from a defect in the ferromagnetic material, and reaches a detection coil, the mechanical wave generates a changing magnetic flux in the detection coil as a result of the inverse magnetostrictive effect. This changing magnetic flux induces an electric voltage within the detection coil that is proportional to the magnitude of the mechanical wave. The transmitting coil and the detection coil can be identical.

Advantages of using the magnetostrictive effect in nondestructive evaluation (NDE) applications include (a) the sensitivity of the magnetostrictive sensors, (b) durability of the magnetostrictive sensors, (c) no need to couple the sensor to the material being investigated, (d) long range of the mechanical waves in the material under investigation, (e) ease of implementation, and (f) low cost of implementation.

The use of magnetostrictive sensors (MsS) in the nondestructive evaluation (NDE) of materials has proven to be very effective in characterizing defects, inclusions, and corrosion within various types of ferromagnetic and non-ferromagnetic structures. A MsS launches a short duration (or a pulse) of elastic guided waves in the structure under investigation and detects guided wave signals reflected from anomalies such as defects in the structure. Since guided waves can propagate long distances (typically 100 feet or more), the MsS technique can inspect a global area of a structure very quickly. In comparison, other conventional NDE techniques such as ultrasonics and eddy current inspect only the local area immediately adjacent to the probes used. Therefore, the use of magnetostrictive sensors offers a very cost effective means for inspecting large areas of steel structures such as strands, cables, pipes, and tubes quickly with minimum support requirements such as surface preparation, scaffolding, and insulation removal. The ability to use magnetostrictive sensors with little preparation of the object under inspection derives from the fact that direct physical contact between the sensors and the material is not required.

Efforts have been made in the past to utilize magnetostrictive sensor technologies in association with the inspection of both ferromagnetic and non-ferromagnetic materials. Included in these efforts are systems described in U.S. Pat. Nos. 5,456,113; 5,457,994; and 5,501,037, which are each commonly owned by the assignee of the present invention. The disclosures of U.S. Pat. Nos. 5,456,113; 5,457,994; and 5,501,037, provide background on the magnetostrictive effect and its use in NDE and are therefore incorporated herein by reference. These efforts in the past have focused primarily on the inspection of pipe, tubing, and steel strands/cables wherein the geometry of the structure is such that the cross-sectional diameter is small in comparison to the length of the structure. While these systems and their application to longitudinal structures find significant applications, there are yet other structures that could benefit from the use of magnetostrictive based NDE.

Other efforts have been made in the past to utilize sensors that measure magnetic flux and/or acoustic waves in structural materials. These efforts have included those described in the following patents:

U.S. Pat. No. 3,555,887 issued to Wood on Jan. 19, 1971 entitled Apparatus for Electroacoustically Inspecting Tubular Members for Anomalies Using the Magnetostrictive Effect and for Measuring Wall Thickness. This patent describes a system designed to direct a mechanical wave through the thickness dimension of a long tubular member. The sensitivity of the device is limited to the directing of a wavefront normal to the surface of the material under inspection and immediately back to a sensor when reflected from an opposite wall or an anomaly.

U.S. Pat. No. 4,881,031 issued to Pfisterer, et al. on Nov. 14, 1989 entitled Eddy Current Method and Apparatus for Determining Structure Defects in a Metal Object Without Removing Surface Films or Coatings. This patent describes a method for establishing localized eddy currents within ferromagnetic materials and recognizes the presence and effect of a coating in order to identify and quantify corrosion beneath the coating. As with other eddy current methods, the ability to inspect a material is limited to the area immediately adjacent to the sensor.

U.S. Pat. No. 5,544,207 issued to Ara, et al. on Aug. 6, 1996 entitled Apparatus for Measuring the Thickness of the Overlay Clad in a Pressure Vessel of a Nuclear Reactor. This patent describes a system directed solely to the measurement of magnetic field variations that result from the distribution of the magnetic field through overlays of varying thickness. The system utilizes a magnetic yoke that is placed in close contact with the surface of the overlay clad of the pressure vessel.

U.S. Pat. No. 5,687,204 issued to Ara, et al. on Nov. 11, 1997 entitled Method of and Apparatus for Checking the Degradation of a Pressure Vessel of a Nuclear Reactor. This patent describes a system similar to the earlier issued Ara, et al. patent and utilizes a magnetic yoke having an excitation coil and a magnetic flux measuring coil that are placed in close contact with the inner wall of the pressure vessel. The hysteresis magnetization characteristics formed by the magnetic yoke and the pressure vessel wall are measured. Degradation of the material comprising the pressure vessel is inferred from a determination of the hardness of the material which is determined from the coercive forces obtained by analyzing the hysteresis characteristics of the magnetization.

The nondestructive evaluation of materials using magnetostrictive sensors is based upon the magnetostrictive effect and its inverse effect, and the phenomenon that causes the physical dimensions of a ferromagnetic material to change slightly when the material is magnetized or demagnetized or otherwise experiences a changing magnetic field. The inverse effect is a phenomenon that causes a magnetic flux in the material to change when the material is stressed. Systems utilizing magnetostrictive sensors use the magnetostrictive effect and its inverse effect to generate and detect guided waves that travel through the ferromagnetic material.

In general, a magnetostrictive sensor consists of a conductive coil and a means for providing a DC bias magnetic field in the structure under inspection. The means for providing a bias magnetic field can include the use of either permanent magnets or electromagnets. In a transmitting magnetostrictive sensor, an AC electric current pulse is applied to the coil. The resulting AC magnetic field (a changing magnetic field) produces elastic waves (also known as guided waves) in an adjacent ferromagnetic material through the magnetostrictive effect. For pipes, cables, tubes, and the like, the waves are launched along the length of the longitudinal structure. In the receiving magnetostrictive sensor, a responsive electric voltage signal is produced in the conductive coil when the elastic waves (transmitted or reflected from anomalies within the material) pass the sensor location, through the inverse magnetostrictive effect.

With MsS techniques, defects are typically detected by using the pulse-echo method well known in the field of ultrasonics. Since the sensor relies on the magnetostrictive behavior found in ferromagnetic materials, this technology is primarily applicable to the inspection of ferromagnetic components such as carbon steel piping or steel strands. It is also applicable, however, to the inspection of nonferrous components if a thin layer of ferromagnetic material, such as nickel, is plated or coupled onto the component in the area adjacent to the magnetostrictive sensors.

The magnetostrictive sensor technique has the advantage of being able to inspect a large area of material from a single sensor location. Such sensors have, for example, been used to accurately inspect a length of pipe or cable of significantly more than 100 feet. Further, magnetostrictive sensor techniques are comprehensive in their inspection in that the methods can detect both internal and external defects, thereby providing a 100% volumetric inspection. The techniques are also quite sensitive, being capable of detecting a defect with a cross-section less than 1% of the total metallic cross-section of cylindrical structures such as pipes, tubes, or rods. Finally, as indicated above, magnetostrictive sensor techniques do not require direct physical contact between the component surface and the sensor itself. This eliminates the need for surface preparation or the use of a couplant.

APPLICATION TO PLATE TYPE AND CONTAINMENT STRUCTURES

In recent years, there have been many reported occurrences of steel liner containment vessels degrading at commercial nuclear power plants. Due to the aging of such facilities and the increased requirements for inspection, incidents of degradation are likely to increase. The structural degradation of these liners, especially corrosion damage, is an important concern since the liners are designed to provide a leak-tight pressure boundary for the nuclear material. Typically, the containment vessels are made from steel sheets welded together. The welds are part of the vessel that should also be inspected.

Many other industrial uses of plate type ferromagnetic materials could benefit from more frequent inspections to determine the state of deterioration, the location of faults, and the likelihood of failure. In most instances in the past, inspections of large plate type objects have required either very expensive off-line inspections or statistical samplings of randomly selected local areas that are for the most part less than reliable. It has heretofore been difficult to carry out a thorough inspection of a plate type structure, or a structure comprised of a plurality of plate type sheets of material welded together, without high cost and long down time for the object under inspection. It would be desirable to use the magnetostrictive sensor technique for detecting and locating various anomaly characteristics within plate type materials. Such techniques could be used for detecting and locating wall thickness reductions in liners, such as those described above, that might be caused by corrosion over time. If such a system were applicable, it would be possible to inspect welds or otherwise inaccessible regions of containment liners and the like that are either imbedded in concrete or adjacent to flooring or equipment that cannot be moved.

It would therefore be desirable to implement magnetostrictive sensor techniques in conjunction with plate type structures in a manner similar to, and with the accuracy of, such systems utilized in conjunction with cylindrical structures to inspect welds in such plate type structures. It would be desirable if an inspection of welds in plate type structures could be carried out in an efficient manner that did not require full access to the surface of the plate. Such a magnetostrictive sensor system would be able to investigate welds in large plate type structures or pipes and would provide a cost effective global inspection of welds in the structure.

In steel mills, coils of relatively thin sheet steel are wound on a drum. Individual coils are joined together by flash butt welding the tail end of the leading coil to the head of a subsequent coil. Flash butt welding involves a rapid heating of coil ends and upset forging of the heated ends. Excess material from the top and bottom of the weld line is trimmed. During the flash butt welding, the joined coils are held stationary for flash butt welding and trimming. At a subsequent inspection station, the flash butt welding is momentarily stopped for non-destructive inspection. If the flash butt welding is good, the joined coils are released for subsequent processing. If a defect is found in the flash butt welding, the coil is moved back to the welding station and the coils are rewelded after removing the bad weld. The entire welding, trimming, and inspection are performed in less than one minute. This is to ensure uninterrupted flow of the downstream operations which can typically reach a flow speed of 30 miles per hour.

During downstream processing, the coil steel is subject to co-rolling, pickling, and annealing, during which time the flash butt welds are subjected to thickness reduction and high tensile stresses. Under these high tensile stresses, a properly made butt weld will often fail causing coil breakage, which interrupts the operation completely. There is a need to have some type of reliable way to inspect the welds to reduce and eliminate coil breakage during downstream operation.

The current method used to inspect the welds is electromagnetic acoustic transducers (EMATs). However, EMAT inspection is not good on sheets more than 2.5 millimeters thick. Also, because the EMAT inspection range is short, the weld joint must be moved out of the welding and trimming machine to a location where the EMAT inspection is performed. If the type of inspection had a longer range, the coil could be inspected while it is still in the welding and trimming machine, thus shortening the process time and increasing productivity.

SUMMARY OF THE PRESENT INVENTION

It is therefore an object of the present invention to provide a method for implementing magnetostrictive based NDE of welds in association with plate type structures and to determine the presence of anomalies indicative of defective welds.

It is a further object of the present invention to provide a method for using magnetostrictive sensors for the inspection of welds in plate type structures that is capable of transmitting and receiving guided waves within the plate type structures and generating signals representative of the characteristics of such waves appropriate for the analysis and detection of anomalies in the welds.

It is a further object of the present invention to provide a method for the inspection of plate type structures and welds therein that includes the use of a magnetostrictive sensor specifically adapted for directing guided waves into the plate type structures and detecting such waves as may be reflected from anomalies within the structure including welding defects.

It is a further object of the present invention to provide a method and apparatus for the nondestructive evaluation of plate type structures and welds therein utilizing magnetostrictive sensors that are capable of investigating large volumes of welded plate type structures without access to the entire surface area of the plates or the welds.

It is yet another object of the present invention to provide a method and apparatus for nondestructive evaluation of welded plate type structures or containments having ferromagnetic materials through the use of a magnetostrictive sensor that may operate either in the symmetrical or anti-symmetrical Lamb wave mode.

It is yet another object of the present invention to provide a method and apparatus for nondestructive evaluation of welded plate type structures utilizing magnetostrictive sensors that generate and detect shear horizontal waves in the item being inspected.

It is yet another object of the present invention to provide a method and apparatus for inspecting electric resistance welding utilizing magnetostrictive sensors.

It is still another object of the present invention to provide a method and apparatus for nondestructive evaluation of pipes and welds therein using magnetostrictive sensors that propagate guided waves in a circumferential direction around the pipe.

Yet another object of the present invention is to provide a method and apparatus for inspecting butt welds in sheet steel using magnetostrictive sensors that propagate guided waves along the length of the sheet.

In fulfillment of these and other objectives, the present invention provides a method and apparatus for implementing magnetostrictive sensor techniques for the nondestructive evaluation of plate type structures such as walls, vessels, enclosures, and the like and welds therein. The system includes magnetostrictive sensors specifically designed for application in conjunction with welded plate type structures that generate guided waves in the plates which travel through the plate in a direction parallel to the surface of the plate. Similarly structured sensors are positioned to detect the guided waves (both incident and reflected) and generate signals representative of the characteristics of the guided waves detected. The system anticipates the use of either discrete magnetostrictive transmitters and receivers or the use of a single magnetostrictive sensor that operates to both transmit and detect the guided waves. The sensor structure is longitudinal in nature and generates a guided wave having a wavefront parallel to the longitudinal direction of the sensor. Appropriate electronics associated with the process of generating the guided waves and controlling the propagation direction of the generated wave through the magnetostrictive transmitter as well as detecting, filtering, and amplifying the guided waves at the magnetostrictive receiver, are implemented as is well known in the art. Signal analysis techniques, also known in the art, are utilized to identify anomalies within the plate type structure and welds therein. The method utilizes pattern recognition techniques as well as comparisons between signal signatures gathered over time from the installation of the structure under investigation to a later point after deterioration and degradation may have occurred.

By rotation of the magnetic field by 90°, the magnetostrictive sensor can be changed from operating in the symmetrical or the anti-symmetrical Lamb wave mode to a horizontal shear wave that is applied to the ferromagnetic material being inspected. In the horizontal shear wave mode, the DC bias magnetic field is in a direction perpendicular to the direction of wave propagation.

The magnetostrictive sensors can also be used to detect defects in electric resistance welding, such as pipes that are welded along a scam thereof. For example, a magnetostrictive transmitter can be placed on one side of the pipe being investigated and a magnetostrictive receiver on the other side of the pipe. By generation of a guided wave around the pipe, any defects in the pipe can immediately be detected, such as in the area of the weld.

Also, the magnetostrictive sensors can be used to detect defects in welding joints between coils of sheet steel. The inspection can occur while the weld joint is still within the welding and trimming machine so that if additional welding and trimming is necessary, it can be performed before the weld joint moves down the processing line. The elastic wave will move in a direction perpendicular to the weld joint so that defects in the weld joint can be more easily determined.

DETAILED DESCRIPTION OF THE PREFERRED EMBODIMENT

Figure 1:
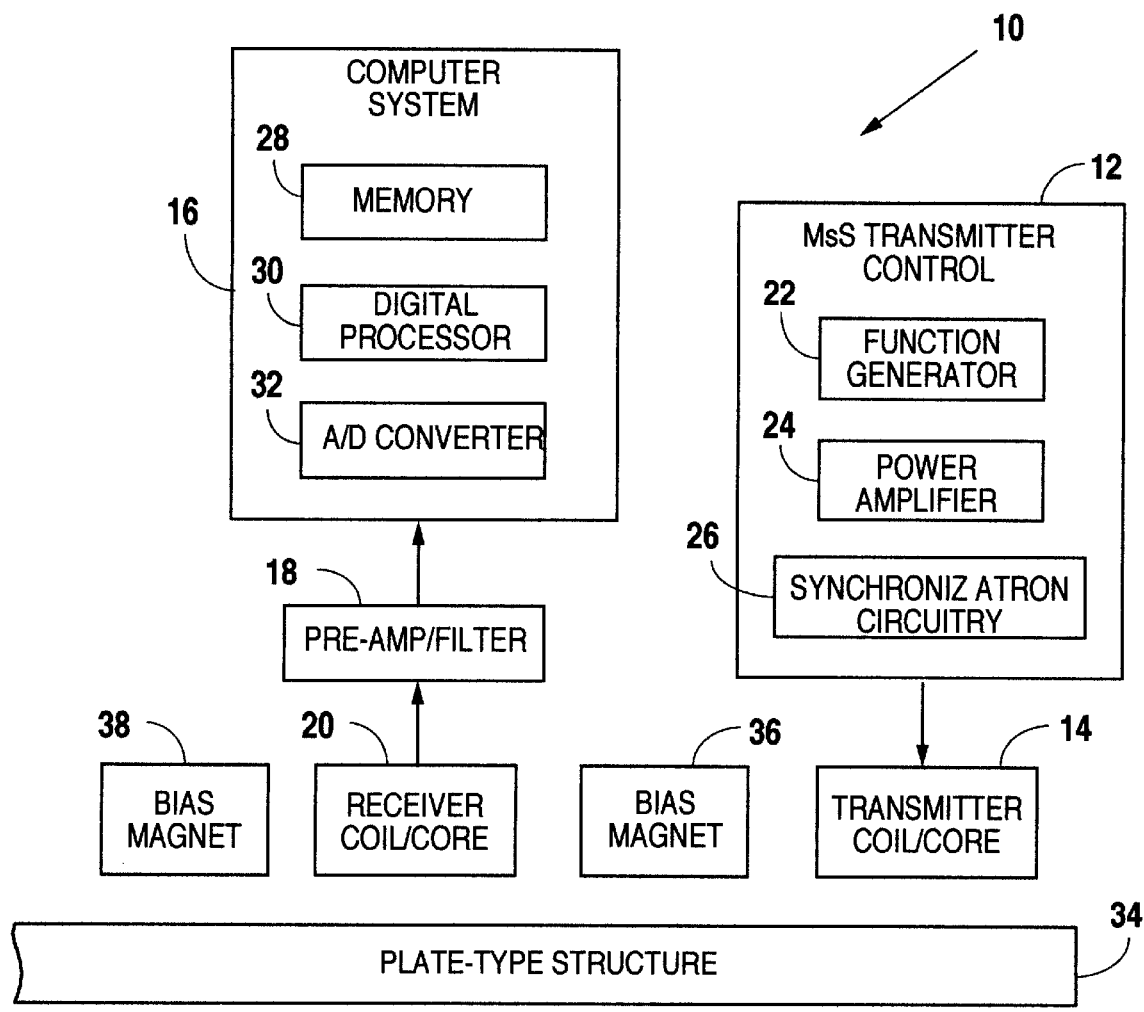
FIG. 1 is a schematic block diagram showing the components of the system of the present invention.

As indicated above, the present invention utilizes the basic methodological approach of earlier developed magnetostrictive sensor techniques associated with the inspection of cylindrical structures such as pipe, tubes, and the like. The basic system of such techniques is combined with a novel magnetostrictive sensor for application to plate type structures. Reference is made first to FIG. 1 for a general description of the complete system utilized to carry on the inspection of a plate type structure. Inspection system 10 includes a magnetostrictive sensor transmitter control 12 and an associated transmitter coil/core 14. Transmitter coil/core 14 is positioned adjacent to the surface of plate type structure 34. Also positioned near the surface of plate type structure 34 is receiver coil/core 20. Receiver coil/core 20 is positioned to detect reflected waves within plate type structure 34 and to thereby generate a signal representative of the wave characteristics that are reflected from a defect present in the structure. Receiver coil/core 20 is connected to preamp/filter 18 which in turn is connected to computer system 16.

Magnetostrictive sensor transmitter control 12 is comprised of function generator 22, power amplifier 24, and synchronization circuitry 26. These elements together generate an appropriate signal for driving transmitter coil/core 14 and thereby generate guided waves within plate type structure 34.

Computer system 16 is comprised of memory 28, digital processor 30, and analog to digital converter 32. These components together receive, digitize, and analyze the signal received from receiver coil/core 20. The signal contains wave characteristics indicative of the characteristics of the reflected guided waves present in plate type structure 34.

Both transmitter coil/core 14 and receiver coil/core 20 have associated with them bias magnets 36 and 38, respectively. Bias magnets 36 and 38 are positioned adjacent the coils/cores 14 and 20 near plate type structure 34 in order to establish a bias magnetic field to facilitate both the generation of guided waves within structure 34 and the appropriate detection of reflected guided waves.

Figure 2:
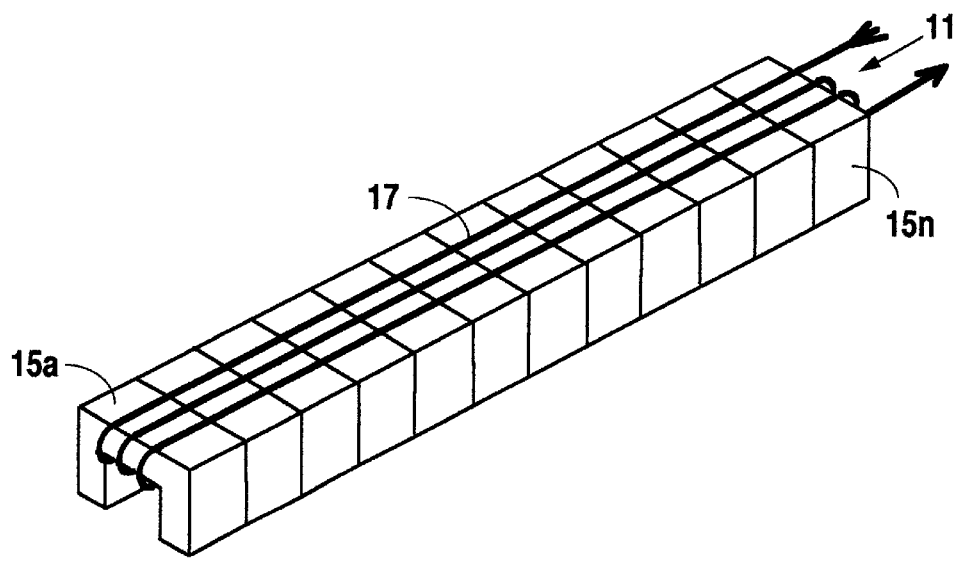
FIG. 2 is a perspective view of a magnetostrictive sensor of the present invention.

Reference is now made to FIG. 2 for a detailed description of the novel magnetostrictive sensor structure utilized in the present invention. Magnetostrictive sensor 11 as shown in FIG. 2 could be utilized as either transmitter coil/core 14 or receiver coil/core 20 described above in FIG. 1. Magnetostrictive sensor 11 is comprised of a plurality of U-shaped cross-sectional cores stacked in a lengthwise direction to form a sensor with a longitudinal axis that is long in comparison to its cross-section. Core elements 15a through 15n in the preferred embodiment may be made from a stack of U-shaped ferrites, transformer steel sheets, mild steel, or permanent magnets. The core elements 15a through 15n could have other shapes; however, U-shaped or E-shaped core elements have been found to be more efficient. If an E-shaped core is used, a transmitter may be located on one part of the E with a receiver on the other part of the E.

Surrounding the stack of U-shaped cores 15a through 15n is wire coil 17. The number of turns for coil 17 is dependent upon the driving current and the magnetic permeability of core 15 and may be varied as is well known in the art.

Figure 3:
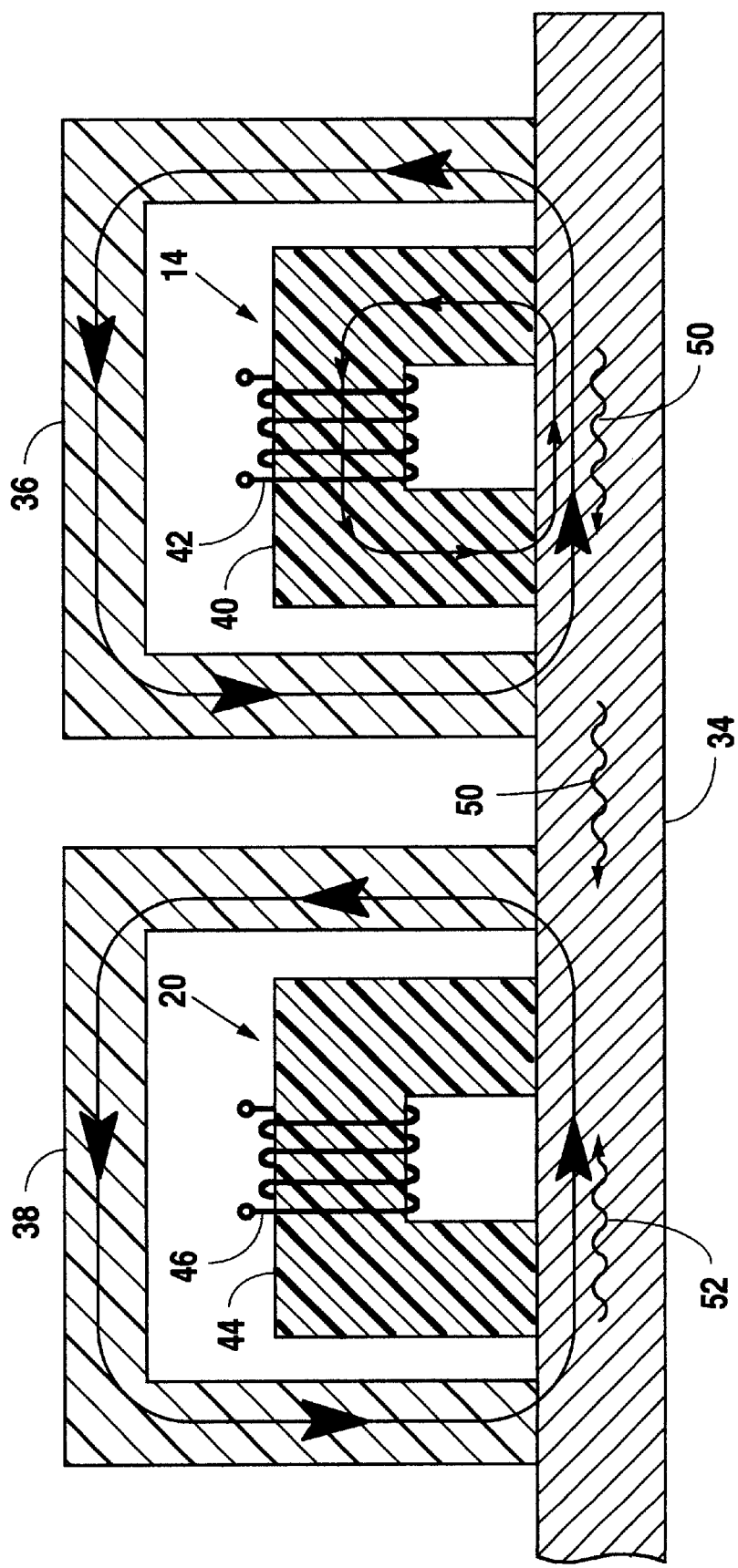
FIG. 3 is a cross-sectional view of the implementation of the sensors of the present invention in conjunction with a plate type structure.

FIG. 3 shows in cross-sectional view the application of a pair of sensors structured as shown in FIG. 2 and implemented in conjunction with the methods of the present invention. In FIG. 3, a cross-section of plate type structure 34 is shown with transmitter coil/core 14 and receiver coil/core 20 positioned on the plate. The view in FIG. 3 of both transmitter coil/core 14 and receiver coil/core 20 is cross-sectional in nature in order to show the establishment of a magnetic flux within plate type structure 34. Associated with each of the coils/cores 14 and 20 are bias magnets 36 and 38. In FIG. 3, bias magnets 36 and 38 are shown placed over coils/cores 14 and 20. It is understood that in the actual implementation of the present invention, bias magnets 36 and 38 may be one or two magnets. What is necessary is that a magnetic field be generated in plate type structure 34 under the transmitter coil/core 14 and the receiver coil/core 20. It is only critical that the DC bias magnetic fields established by bias magnets 36 and 38 are established within the volume of plate type structure 34 under transmitter coil/core 14 and under receiver coil/core 20 as appropriate.

Transmitter coil/core 14 is comprised of core material 40 and coil windings 42. Together these components, as driven by the magnetostrictive sensor transmitter control (not shown), operate to generate changes in the magnetic field established by bias magnet 36 within plate type structure 34. This time-varying or AC magnetic field within plate type structure 34 generates a mechanical, guided wave that propagates in a direction parallel to the surface of plate type structure 34. This guided wave is depicted as wave 50 in FIG. 3 and propagates in a direction away from transmitter coil/core 14. If, as shown in FIG. 3, transmitter coil/core 14 is placed on the surface of plate type structure 34, with the longitudinal axis of coil/core 14 directed into the drawing page in the view shown, wave 50 would propagate in two directions away from the longitudinal axis of coil/core 14 and through plate type structure 34. This would serve to investigate the volume of plate type structure 34 bounded by the length (long axis) of the magnetostrictive sensor utilized. In this manner, an inspection "sweep" of a volume of plate type structure 34 can be carried out generally equal in width to the length of the magnetostrictive sensor.

The arrangement of the magnetostrictive sensor utilized as the detection coil in the present invention is essentially the same as the arrangement for the transmitter coil. In FIG. 3, receiver coil/core 20 is comprised of core material 44, shown in cross-section, as well as coil windings 46. Bias magnet 38 is likewise positioned over receiver coil/core 20. This arrangement establishes a bias magnetic field within plate type structure 34 that fluctuates according to the presence of reflected mechanical guided waves within the material adjacent the sensor. In FIG. 3, reflected mechanical waves are depicted as 52 proximate to receiver coil/core 20 and are detected thereby. In this manner, mechanical waves passing through plate type structure 34 under receiver coil/ core 20 are detected and "translated" into voltage fluctuations in coil 46 in a manner that generates an appropriate signal for analysis by the balance of the electronics of the system of the present invention (not shown).

As indicated above, the methods and apparatus of the present invention can be utilized in conjunction with discrete magnetostrictive transmitters and receivers or in conjunction with a single magnetostrictive sensor operable as both a transmitter and a receiver. In the latter case, the structures described in FIG. 3 would be limited to a single magnetostrictive sensor of the configuration shown for either transmitter coil/core or receiver coil/core 20.

In another alternative approach, one with greater practical application, two transmitter sensors and two receiver sensors may be used when the sensors are controlled by appropriate phasing. In this manner, the direction of the interrogating beam may be controlled. As an example, when the transmitter generates the wave in a first position (+) direction, the return signals may be detected by a receiver controlled to detect waves traveling in the negative (−) direction. As mentioned above, this control is achieved by phasing the two sensors appropriately, a process well known in the field of NDE techniques. In this manner, an inspection of the plate may be carried out first to one side of the transmitting sensor and then by simply switching the sensor instrumentation an inspection may be carried out to the opposite side of the transmitting sensor. Various other inspection techniques known and used with magnetostrictive sensors may likewise apply with the methods and structures of the present invention.

Figure 4:
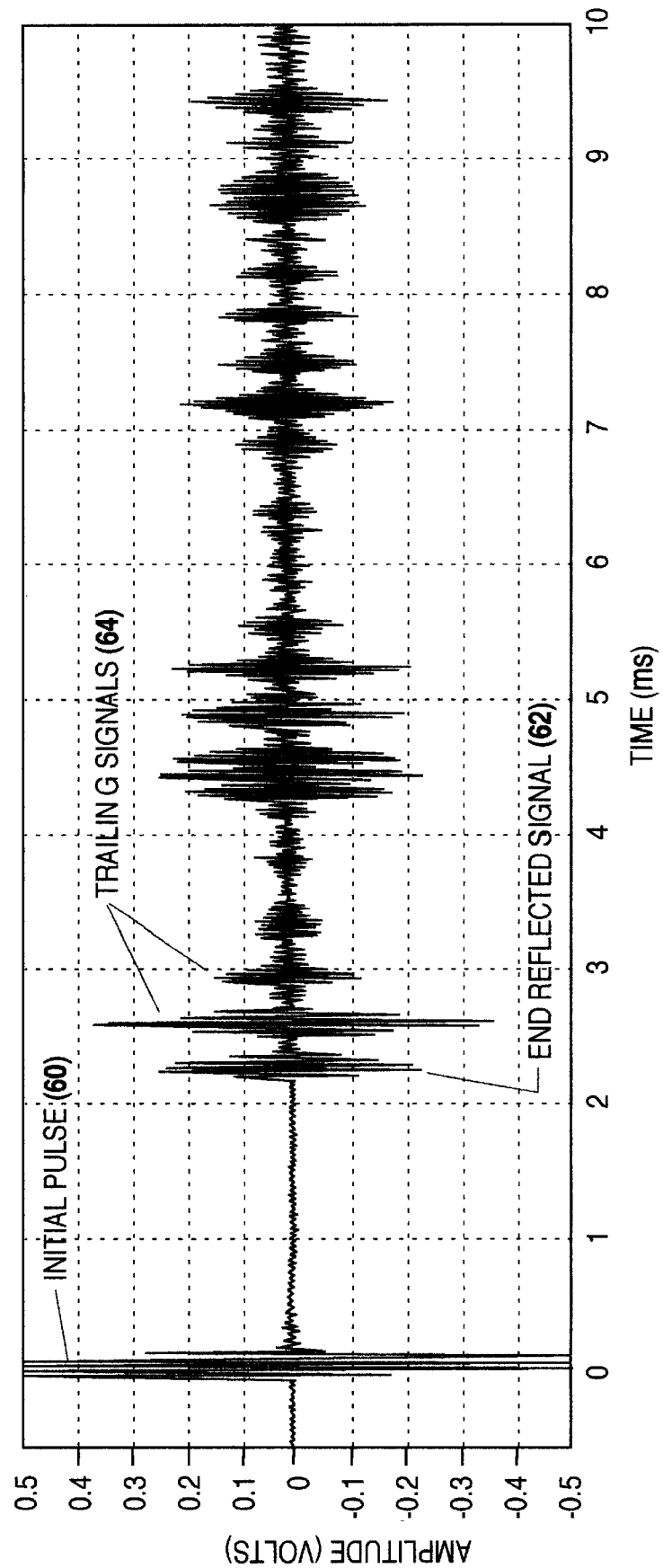
FIG. 4 is a plot of a signal received through the system of the present invention utilizing a 60 kHz $S_0$ wave mode signal in a 4 foot wide, 20 foot long, 0.25 inch thick steel plate.
Figure 5:
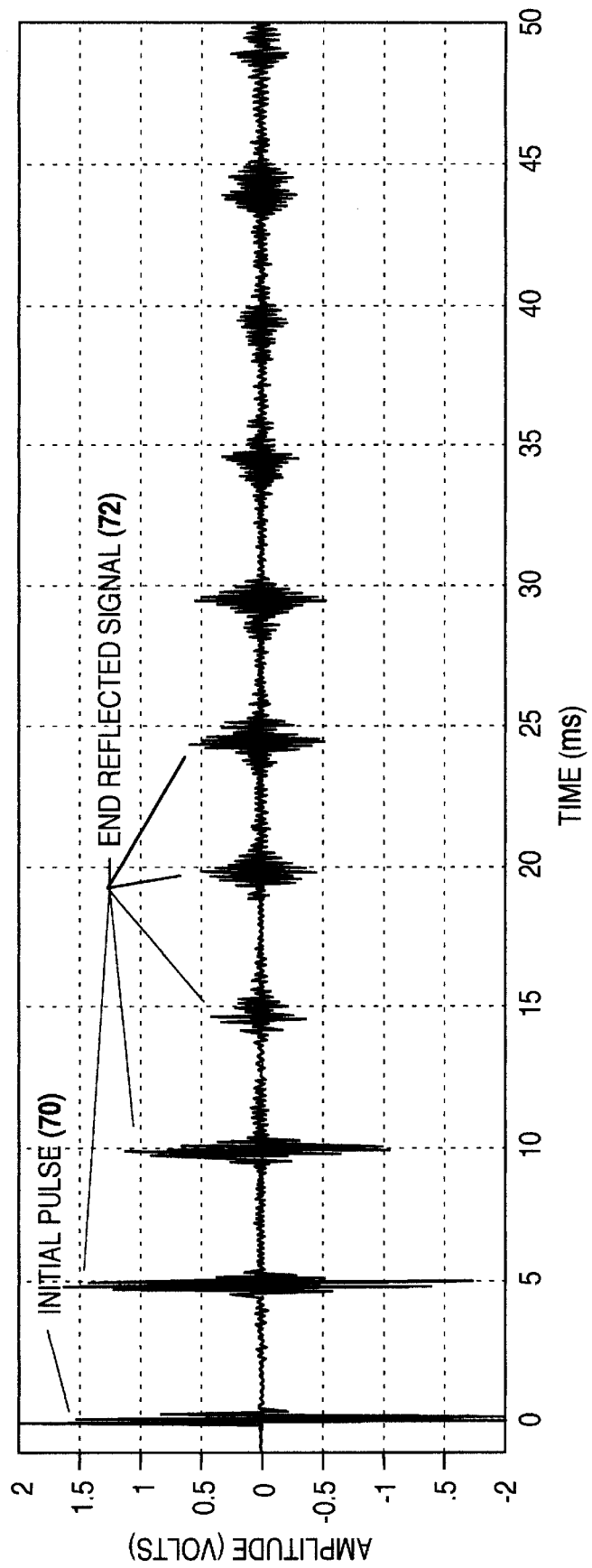
FIG. 5 is a plot of a signal received through the system of the present invention in conjunction with the structure associated with FIG. 4 for a 40 kHz $A_0$ wave mode signal.

Reference is now made to FIGS. 4 and 5 for a detailed description of sample data acquired from a 0.25 inch thick, 20 foot long, and 4 foot wide steel plate investigated by the devices and methods of the present invention.

The signal represented in FIG. 4 shows the first symmetric wave mode ($S_0$) in the plate while the signal depicted in FIG. 5 shows the first anti-symmetric wave mode ($A_0$). FIG. 4 is a time varying amplitude plot of a 60 kHz magnetostrictive sensor signal taken from the above described steel plate geometry. The wave is directed through appropriate orientation of the sensor and propagates in the long direction within the steel plate. The signal components identified in FIG. 4 include the initial pulse 60, end reflected signal 62, and trailing signals 64. Likewise in FIG. 5, initial pulse 70 is indicated, as are end reflected signals 72.

Anomalies within the path of the guided wave generated within the material would, as is known in the art, generate signal components having amplitudes sufficient for identification within either of the two signals shown in FIGS. 4 and 5. In this manner, characteristics of anomalies detected within the plate type structure can be identified and located in the direction of wave propagation away from the magnetostrictive sensor. As is known in the art, the relative location of an anomaly may be identified by the position of the signal characteristic indicative of the anomaly in time relationship with the initial pulse (indicative of the position of the sensor) and the end reflected signals 62 and 72.

Figure 6:
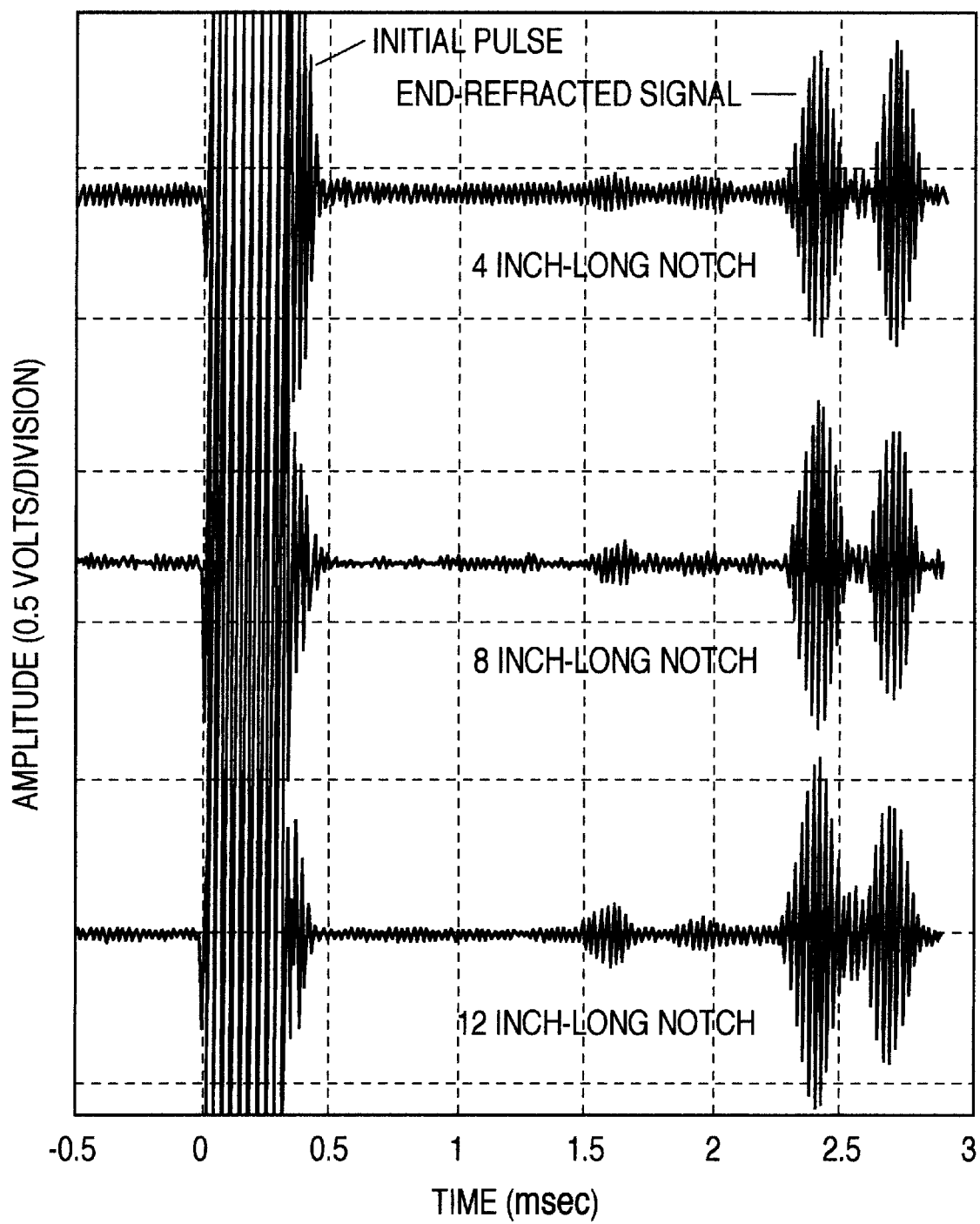
FIG. 6 is a plot of three signals received through the system of the present invention utilizing a 40 kHz $S_0$ wave mode signal in a 4 foot wide, 20 foot long, 0.25 inch thick steel plate.
Figure 7:
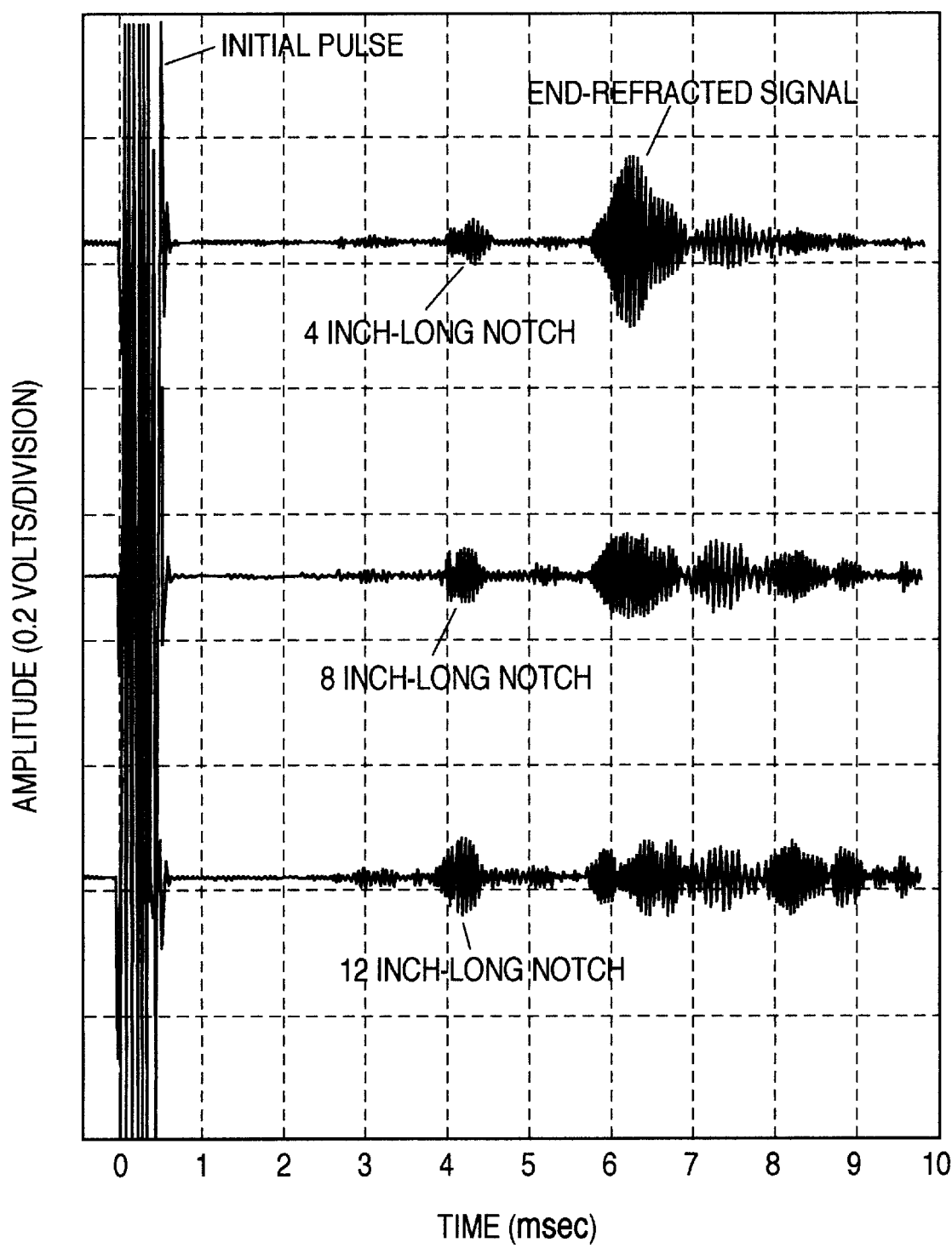
FIG. 7 is a plot of three signals received through the system of the present invention utilizing a 20 kHz $A_0$ wave mode signal in a 4 foot wide, 20 foot long, 0.25 inch thick steel plate.

Examples of such signals are shown in FIGS. 6 and 7. FIG. 6 shows pulse-echo magnetostrictive sensor data for a 40 kHz $S_0$ wave mode signal obtained in a 4 foot wide, 20 foot long, 0.25 inch thick steel plate. Three signals are shown for data collected with a 4 inch long, 8 inch long, and 12 inch long notch cut in the plate at a point approximately two-thirds of the length of the plate away from the sensor.

FIG. 7 shows pulse-echo magnetostrictive sensor data for a 20 kHz $A_0$ wave mode signal obtained in a 4 foot wide, 20 foot long, 0.25 inch thick steel plate. Three signals are also shown for data collected with a 4 inch long, 8 inch long, and 12 inch long notch cut in the plate at a point approximately two-thirds of the length of the plate away from the sensor.

In each case, the notch is not only detectable but may be characterized as to size and position. Various signal analysis techniques may be applied to these signals to discern and characterize other types of anomalies found in such plate-type structures. Discrete fractures and the like are typically identified by isolated reflected waves, while broad deteriorations or corrosions in the plate might be identified by grouped waves received over a period of time. In addition, it is anticipated that signature signals of a particular plate type structure might be acquired prior to implementation of the structure into service. In this manner subsequent signatures may be acquired periodically and compared with the initial base line reference signature to determine the presence of developing anomalies within the plate.

To prove the invention works, symmetric ($S_0$) and anti-symmetric ($A_0$) longitudinal wave mode signals were generated and detected using a 12 inch long magnetostrictive probe such as shown in FIG. 2. To generate and detect these wave modes, the bias magnets 36 and 38 are applied in the direction parallel to the direction of wave propagation (perpendicular to the lengthwise length of the magnetostrictive probe). The same probe as shown in FIG. 2 can be used to generate and detect shear horizontal waves in a plate by applying DC bias magnetic fields in a direction perpendicular to the wave of propagation (or parallel to the lengthwise direction of the magnetostrictive probe).

Figure 8A:
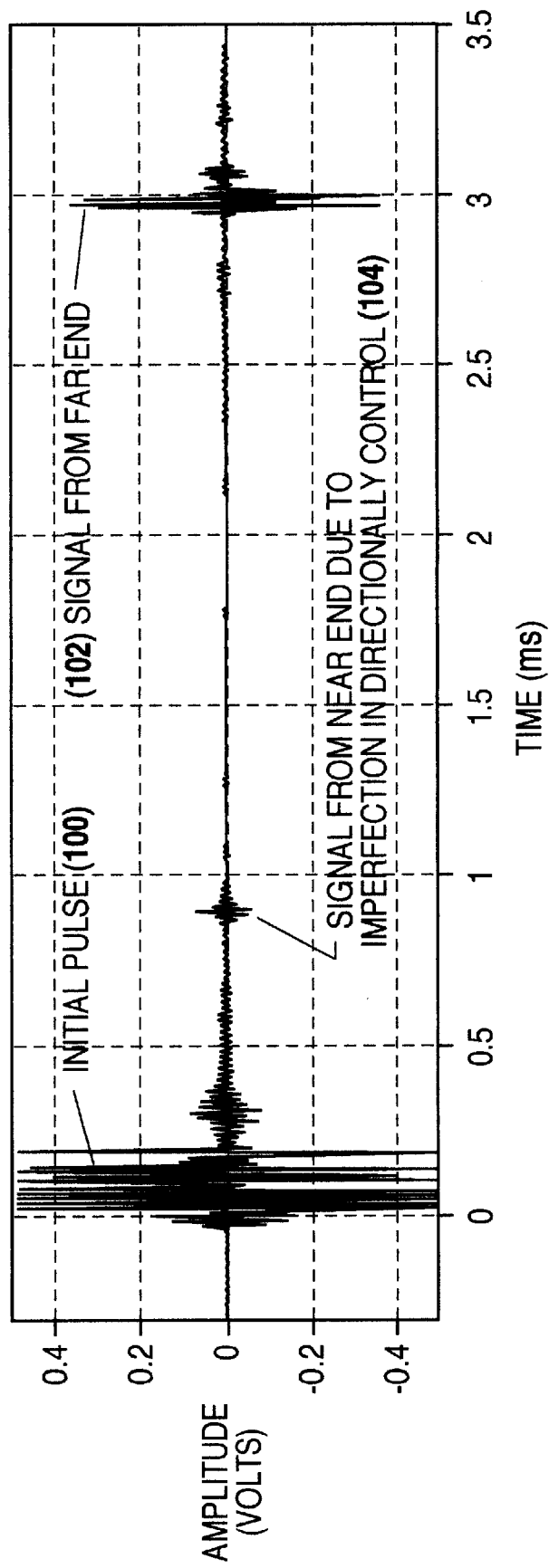
FIGS. 8(a) and (b) are a plot of a shear horizontal wave received through the system of the present invention utilizing an 80 kHz shear horizontal wave in a 4 foot wide, 20 foot long 0.25 inch thick steel plate, before and after a 0.25 inch hole is cut therein.
Figure 8B:
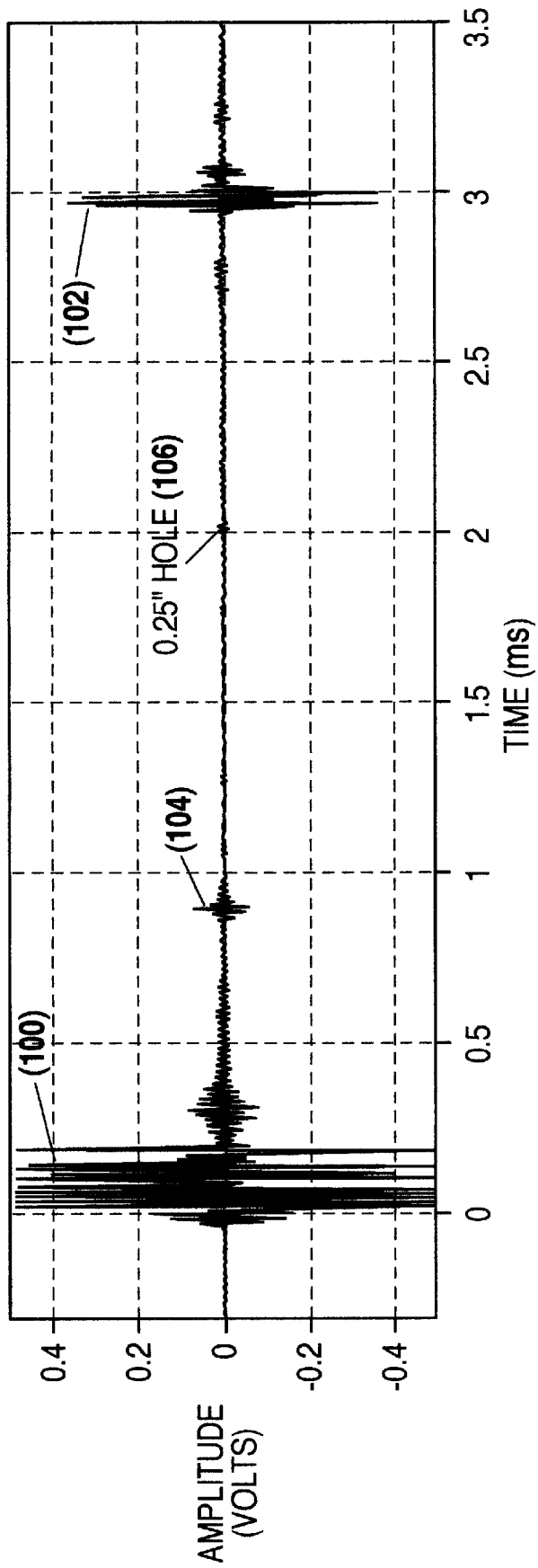

Using a 4 inch long magnetostrictive probe, a signal was induced in a 0.25 inch thick, 4 foot wide, 20 feet long, steel plate. FIG. 8(*a*) shows the signal as generated and reflected over time. The initial pulse 100 is generated by the magnetostrictive transmitter controller 12 until it reaches the far end of the sheet and a signal from the far end 102 is received by the receiver coil/core 20. A signal from the near end 104 is received due to the imperfect directionality control of the system.

After drilling a 0.25 inch hole about two-thirds of the way down the sheet, another initial pulse 100 is sent down the sheet. Again, a signal is received from the near end 104 due to imperfect directionality control. Also, a signal 102 from the far end is received. However, now a signal 106 is received that indicates the 0.25 inch hole in the sheet. Therefore, FIGS. 8(*a*) and (*b*) in combination clearly illustrate that shear horizontal waves can be used in the magnetostrictive inspection techniques and probes of the current invention. Also, the magnetostrictive testing of the large plate structures is suitable for low frequency operation (200 kHz or less), has good sensitivity and long range inspection, and is relatively tolerate to liftoff. This is not the case if the inspection technique had used other common nondestructive evaluation techniques, such as electromagnetic acoustic transducers.

Figure 9:
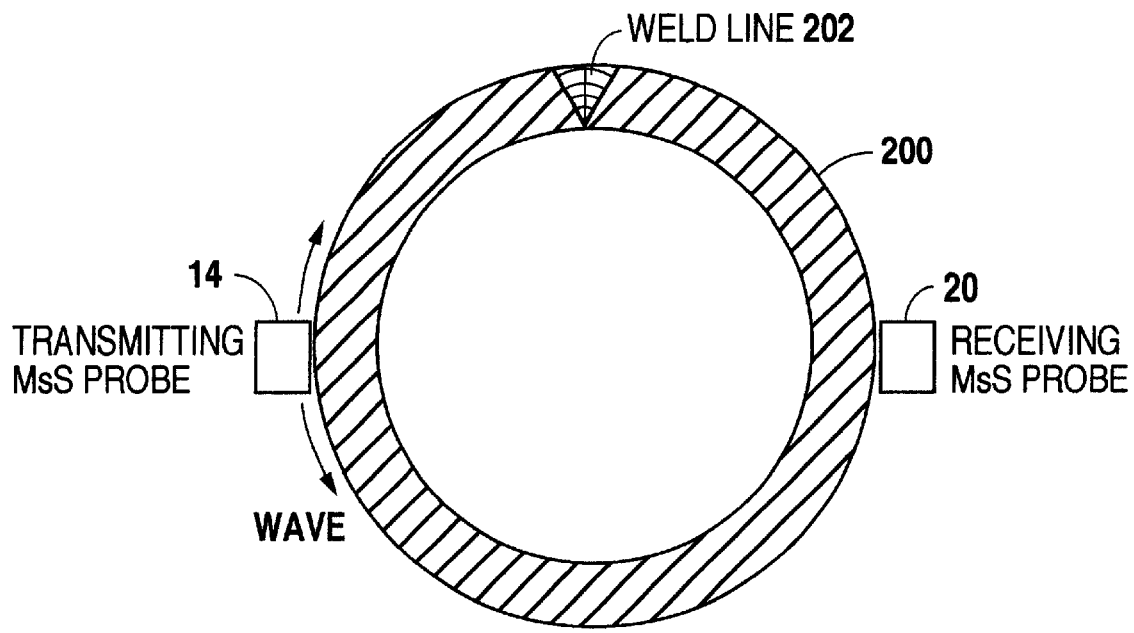
FIG. 9 is a pictorial end view of a welded pipe being inspected using a magnetostrictive transmitting probe and a magnetostrictive receiving probe on opposite sides of the pipe.
Figure 10A:
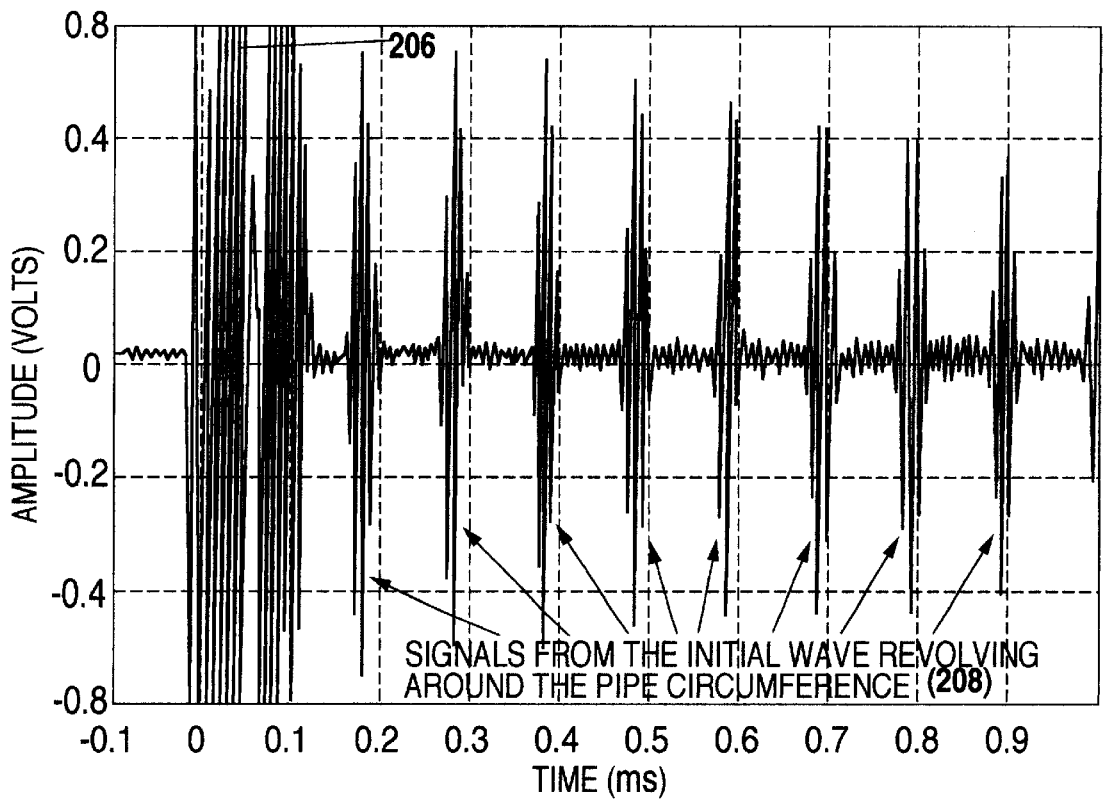
FIGS. 10(a) and (b) are plots of signals received through the system of the present invention when used to test the large diameter pipe as shown in FIG. 9, utilizing a 150 kHz shear horizontal wave mode in a 4.5 inch outside diameter steel pipe having a 0.337 inch thick wall before and after cutting a notch therein.

Pipes can be considered as plates that are simply bent in a circle. Pipes are literally made from sheet metal that is bent into a circle and welded on one side thereof utilizing electric resistance welding. Magnetostrictive inspection techniques may be used to inspect such pipes as shown and explained in connection with FIG. 9, including the electric resistance welding. A pipe 200 is shown with a weld line 202. A transmitter coil/core 14 is located on one side of the pipe 200 and a receiver coil/core 20 is located 180° on the opposite side of the large diameter pipe 200. While not shown, magnetic bias is provided adjacent to the transmitter coil/ core 14 and the receiver coil/core 20. Using the inspection system 10 as shown in FIG. 1, an initial pulse 206 is started around the pipe as shown in FIG. 10(a). Each time the pulse passes the receiver coil/core 20, a signal 208 is received. The signal 208 dies out over a period of time and after repeated revolutions around the pipe 200.

If the transmitter coil/core 14 is 180° around the pipe 200 from the receiver coil/core 20, the two opposite going waves add constructively producing a single large amplitude signal. Once generated, the wave keeps revolving around the circumference of the pipe 200 until all of its energy is dissipated. Therefore, the generated wave produces signals at regular intervals which are equal to the transient time of the shear horizontal wave to travel around the full circumference of the pipe 200. If there are any defects at the weld line 202, they will clearly be indicated as defect signals. If the weld line is approximately 90° from transmitter coil/core 14, then the defect would be approximately midway between the signals 208 as received by the receiver coil/core 20.

To prove the measuring of the defects, the applicant, after measuring the signal as shown in FIG. 10(a), cut a notch in the pipe 200. The test was then repeated with an initial pulse 206 inducing a shear horizontal wave around the circumference of the pipe 200. Again, signals 208 indicate each time the shear horizontal wave reaches the receiver coil/core 20. However, in addition, there are notch signals 210 that are created by a reflected signal from the notch that has been induced in the pipe 200. The notch signal 210 increases in amplitude with time because each time the initial wave revolves around the pipe 200, it passes the notch defect thereby producing a notch defect signal 210 which is then added to the previous notch defect signal 210. The increasing of the notch signal 210 occurs for a period of time and then it will decrease until its energy is dissipated, the same as signal 208.

Figure 10B:
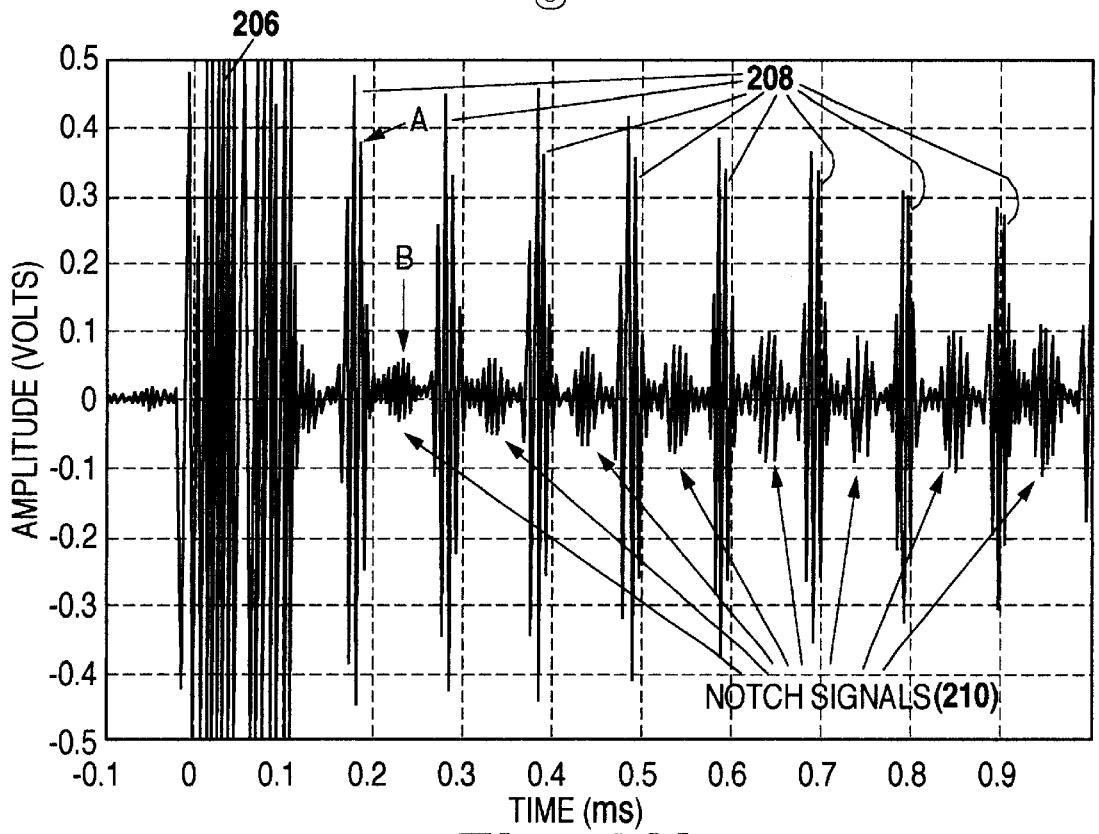

It is possible to get a comparative indication as to the size of the defect by the ratio between the first initial wave signal amplitude 208 and the first defect signal amplitude 210. In the example illustrated in FIG. 10(b), the notch is approximately 8% of the cross-sectional area. This compares well to the ratio of signal 208 to 210 being approximately 10%. This is intended to be a rough generalization as to the size of the notch. Obviously, other factors would be considered, such as whether the notch is perpendicular or parallel to the direction of travel of the shear horizontal wave.

By use of the method as just described, the present invention can be used to inspect pipes for longitudinal defects and corrosion defects. In the present method, the magnetostrictive probes are moved along the length of pipe to determine any defects in the pipe. In manufacturing facilities, the magnetostrictive transmitters or receivers may be stationary with the pipes moving therebetween and simultaneously being inspected for any defects.

While one of the advantages of the present invention is the ability to carry out broad inspections of large volumes of a plate type structure from a single positioning of the sensor, it is anticipated that the complete investigation of a containment vessel or the like would require multiple placements of the sensor in a variety of positions and orientations. For example, a containment vessel might require the placement of the sensor in a sequential plurality of positions along a predetermined scan line (which could be either horizontal or vertical to the floor) that best achieves the inspection of the entire structure. In this manner, a progressive inspection of an entire containment vessel is carried out without the requirement that all surfaces of the vessel be accessed.

Figure 11:
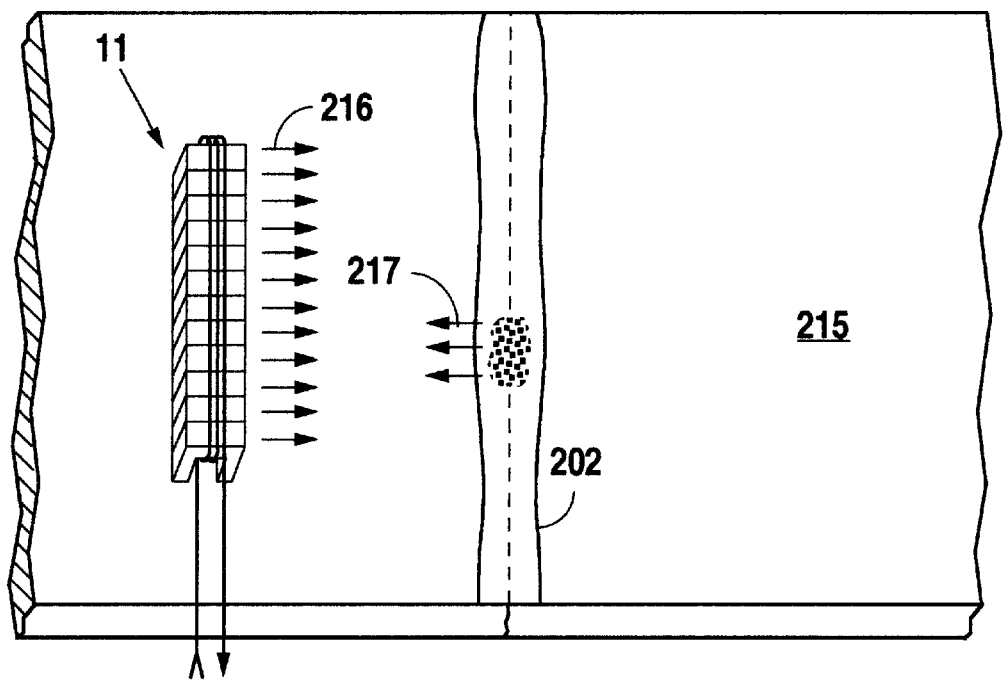
FIG. 11 is a pictorial perspective view of a magnetostrictive sensor being used to inspect butt welding joints.

Another very practical application of the present invention is in the continuous processing of coils of relatively thin sheet steel wound on a drum during the manufacturing process in steel mills. Magnetostrictive sensors 11 can be used to inspect butt weld lines 202 for continuous steel-coil processing lines. FIG. 11 is a pictorial perspective view of a magnetostrictive sensor 11 being used to inspect butt weld lines 202 in steel mills. At a location outside the welding and trimming machine, the magnetostrictive sensor transmitting coil/core 12 (See FIG. 3) and receiving coil/core 20 (See FIG. 3) are positioned parallel to the weld line 202 so that the guided wave 216 beam by the transmitting coil/core 14 is normal to the weld line 202. The magnetostrictive sensor transmitting coil/core 14 and receiver coil/core 202 (which can be one magnetostrictive sensor 11) are placed over the steel sheet 215 with a suitable liftoff distance of preferably 2 mm to 5 mm.

A suitable level of bias magnetic field is applied to the steel sheet 215 for the magnetostrictive sensor 11 to operation. The magnetization bias is provided by the U-shaped electromagnetic or permanent magnetic 15a through 15n as described in conjunction with FIG. 2. Third, immediately after the trimming operation and during release of the clamps holding the steel sheet 215 in place for the welding and trimming operations, a short pulse of guided wave 216 is generated in the steel sheet 215 by exciting the transmitting coil/core 14 with a short pulse of electric current. In contrast to the EMAT's, which use sheer horizontal waves in frequencies over 250 kHz, this embodiment uses the first symmetric ($S_0$) or the first antisymmetric ($A_0$) waves under 200 KHz.

The reflected waves 217 are detected from weld defects using the receiving coil/core 20. The reflected waves 217 are amplified using a suitable signal amplifier and the data is obtained as shown in FIG. 1.

The steps are repeated while moving the coil/cores 14 and 20 parallel to the weld line 202 so that the entire length of the weld is examined. The acquired data is displayed as a function of scan position and saved in a computer. The whole process is performed while the clamps are released and lasts only a few seconds.

The acquired data is provided to the welding machine control unit so that an appropriate follow up action can be taken automatically. For example, if no defect signal is detected that exceeds a certain threshold level, the welded sheets are set in motion for continuous processing. If a defect signal exceeding a threshold level is detected, the welded sheets are clamped again for cutting and rewelding while giving a warning signal to the welding machine operator.

Instead of physically moving of the coil/cores 14 and 20 across the steel sheet 215 width in a scanning type motion, electronic scanning can be used by employing a multiplexer and an array of magnetostrictive sensor transmitting 14 and receiving coil/cores 20 covering the entire steel sheet 215 width. The latter approach would be better since it would have no moving parts. In laboratory investigations, the magnetostrictive sensor coil/cores 14 and 20 have already shown good sensitivity in steel plates 6.35 mm thick. Also the inspection range of the magnetostrictive sensor coil/cores 14 and 20 have been shown to be more than 15 meters. In addition, the magnetostrictive sensor coil/cores 14 and 20 have good tolerance to liftoff distance (can be more than 5 mm) and are much sturdier and durable physically than EMAT's.

Although a description of a preferred embodiment of the apparatus and method of the present invention has been described, it is anticipated that variations in the manner in which the basic sensor structure of the present invention may be utilized are possible. No specific dimensions for the sensor structure described have been identified as such would be dependent upon the specific plate type structures to be investigated. It is anticipated that sensors of a variety of lengths could be utilized depending upon the requirements of the environment of investigation. In general, the basic structure of the sensor described in the present invention may be utilized wherever ferromagnetic plate material is utilized. In such instances where encircling coil type magnetostrictive sensors would not be appropriate, the sensor structure of the present invention provides a mechanism whereby the sensitivity and accuracy of the magnetostrictive investigation technique can be carried out. It is anticipated that other applications of the basic sensor structure described herein will be discerned by those skilled in the art of nondestructive evaluation of materials.

What is claimed is:

1. A method for nondestructive inspection of a weld in a plate type ferromagnetic structure, whether flat or curved, for defects in the weld using magnetostrictive techniques, said method comprising the following steps:

first locating a transmitter with an elongated axis adjacent to said plate type ferromagnetic structure, said elongated axis of said transmitter being generally parallel to said weld;

providing a first DC bias magnetic field in said plate type ferromagnetic structure near said transmitter;

second locating a receiver with an elongated axis adjacent to said plate type ferromagnetic structure, said elongated axis of said receiver being generally parallel to said weld;

providing a second DC bias magnetic field in said plate type ferromagnetic structure near said receiver;

generating a pulse signal in a transmitter control circuit and delivering said pulse signal to said transmitter, said transmitter creating a magnetostrictive wave front in said ferromagnetic structure, said magnetostrictive wave front traveling perpendicular towards said weld;

detecting by said receiver said magnetostrictive wave front and any reflected signals, including those caused by defects in said weld of said plate type ferromagnetic structure; and determining if said reflected signals were due to defects in said weld in said plate type ferromagnetic structure;

said transmitter and said receiver having a core and a coil wound lengthwise therearound along said elongated axis thereof so that said wave front is parallel to said elongated axis and moves perpendicular thereto.

2. The method for nondestructive inspection of a weld in a plate type ferromagnetic structure using magnetostrictive techniques of claim 1 wherein said transmitter and said receiver are a single item and said first DC bias magnetic field and said second DC bias magnetic field are the same.

3. The method for nondestructive inspection of a weld in a plate type ferromagnetic structure using magnetostrictive techniques of claim 1 wherein said elongated axis of said transmitter and said receiver are generally parallel to each other.

4. The method for nondestructive inspection of a weld in a plate type ferromagnetic structure using magnetostrictive techniques of claim 3 wherein said elongated axis is at least multiples of a width of said core.

5. The method for nondestructive inspection of a weld in a plate type ferromagnetic structure using magnetostrictive technique of claim 4 wherein said wave front is selected from the group consisting of symmetric, anti-symmetric or shear horizontal waves.

6. The method for nondestructive inspection of a weld in a plate type ferromagnetic structure using magnetostrictive techniques of claim 4 wherein said core is made from a stack of U-shaped cores, length of said elongated axis being determined by how many of said U-shaped cores are in said stack, said coil being wound lengthwise around said stack.

7. The method for nondestructive inspection of a weld in a plate type ferromagnetic structure using magnetostrictive techniques of claim 1 wherein said pulse is less than 200,000 cycles per second.

8. The method for nondestructive inspection of a weld in a plate type ferromagnetic structure using magnetostrictive techniques of claim 1 that has good sensitivity, a long inspection range and is relatively tolerant to liftoff by said transmitter or said receiver.

9. The method for nondestructive inspection of a weld in a plate type ferromagnetic structure using magnetostrictive techniques of claim 4 wherein said core is made from a stack of C-shaped cores, length of said elongated axis being determined by how many of said C-shaped cores are in said stack.

10. The method for nondestructive inspection of a weld in a plate type ferromagnetic structure using magnetostrictive techniques of claim 1 further including a plurality of said transmitter whose elongated axis are generally parallel to create said wave front broad enough to cover a width of said plate type ferromagnetic structure.

11. The method for nondestructive inspection of a weld in a plate type ferromagnetic structure using magnetostrictive techniques of claim 10 further including a plurality of said receiver whose elongated axis are generally parallel, said plurality of said receivers being broad enough to detect said reflected signal across said width of said plate type ferromagnetic structure.

12. The method for nondestructive inspection of a weld in a plate type ferromagnetic structure using magnetostrictive techniques of claim 11 wherein said transmitters and said receivers are combined and said first DC bias magnetic field and said second DC bias magnetic field are combined.

* * * * *